US00PP29702P3

(12) United States Plant Patent
Kordes

(10) Patent No.: US PP29,702 P3
(45) Date of Patent: Sep. 25, 2018

(54) MINIATURE ROSE PLANT NAMED 'KORPOT066'

(50) Latin Name: *Rosa hybrida*
Varietal Denomination: KORpot066

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 15/530,437

(22) Filed: Jan. 13, 2017

(65) Prior Publication Data

US 2017/0208715 P1 Jul. 20, 2017

Related U.S. Application Data

(60) Provisional application No. 62/388,203, filed on Jan. 19, 2016.

(51) Int. Cl.
*A01H 5/02* (2018.01)

(52) U.S. Cl.
USPC ..... Plt./122

(58) Field of Classification Search
USPC ..... Plt./122, 121, 116, 123, 128, 129, 151
CPC ..... A01H 5/0222; A01H 5/0831; A01H 5/02; A01H 5/00; A01H 6/749
See application file for complete search history.

(56) References Cited

U.S. PATENT DOCUMENTS

PP15,716 P2 * 4/2005 Kordes ..... A01H 5/0222 Plt./121

* cited by examiner

*Primary Examiner* — June Hwu
(74) *Attorney, Agent, or Firm* — Samuel R. McCoy, Jr.

(57) ABSTRACT

'KORpot066' is a new and distinct variety of *Rosa hybrida* which is characterized by the combination of an upright to bushy growth habit, moderately vigorous growth, and an abundance of large, very double flowers with an intense hot pink general tonality. The new variety propagates successfully by stem cuttings and has shown to be uniform and stable in the resulting generations from asexual propagation.

1 Drawing Sheet

Latin name of genus and species: The Latin name of the genus and species of the novel variety disclosed herein is *Rosa hybrida.*

Variety denomination: The inventive variety of *Rosa hybrida* disclosed herein has been given the variety denomination 'KORpot066'.

STATEMENT REGARDING PRIOR DISCLOSURES BY THE INVENTOR UNDER 37 C.F.R. 1.77(B)(6)

The first public disclosure of the claimed plant was made by the inventor on Jan. 27, 2015 at an industry tradeshow in Essen, Germany. Plants were not available for purchase for some months after this public disclosure. 'KORpot066' was not publically available or sold prior to the one year anniversary of the filing date of the provisional application to which benefit is claimed.

BACKGROUND OF THE INVENTION

The present invention relates to a new and distinct *Rosa hybrida*, miniature rose cultivar, which has been given the variety denomination of 'KORpot066'. Its market class is miniature rose.

Parentage: The *Rosa hybrida* cultivar 'KORpot066' originated as a naturally occurring mutation of *Rosa hybrida* 'KORpot042' (U.S. patent application Ser. No. 14/544,576; application abandoned). 'KORpot066' was discovered in March of 2014, in a greenhouse, at the inventor's nursery in Offenseth-Sparrieshoop, Germany. 'KORpot066' was discovered by Tim-Hermann Kordes as a branch mutation and was selected for its intense hot pink flowers.

Asexual Reproduction: The first asexual propagation of 'KORpot066', by way of stem cuttings, was performed in April of 2014 at the inventor's nursery in Offenseth-Sparrieshoop, Germany. Subsequently, 'KORpot066' has been successfully propagated by stem cuttings in Jackson County, Oreg. These initial and other subsequent propagations conducted in controlled environments demonstrate that 'KORpot066' reproduces true to type in successive generations of asexual reproduction.

SUMMARY OF THE INVENTION

The following characteristics have been repeatedly observed and represent the distinguishing characteristics of the new *Rosa hybrida* cultivar 'KORpot066'. These traits, in combination, distinguish 'KORpot066' as a new and distinct cultivar.

1. *Rosa hybrida* 'KORpot066' exhibits an upright to bushy growth habit; and
2. *Rosa hybrida* 'KORpot066' exhibits moderately vigorous growth; and
3. *Rosa hybrida* 'KORpot066' exhibits a very double petal count; and 4. *Rosa hybrida* 'KORpot066' exhibits a large flower size for a miniature rose; and
5. *Rosa hybrida* 'KORpot066' exhibits an intense, hot pink flower color at anthesis.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORpot066', taken from fifteen month old plants.

DETAILED BOTANICAL DESCRIPTION

The following is a detailed botanical description of a new and distinct variety of *Rosa hybrida* known as 'KORpot066', based upon field observations made in October of 2016, from fifteen month old container-grown plants in a greenhouse environment in Jackson County, Oreg. Those skilled in the art will appreciate that certain characteristics will vary with older or, conversely, with younger plants. 'KORpot066' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2001 edition except where common terms of color are used.

A botanical description of 'KORpot066' and comparisons with other varieties of *Rosa hybrida* are provided below.

General plant description:

*Growth rate*.—Moderately vigorous.

*Growth habit*.—Upright to bushy.

*Mature dimensions*.—25 to 30 cm tall and 20 to 22 cm wide, on average, when grown as a 15 cm nursery pot.

*Cold hardiness*.—Unknown.

*Propagation*.—Stem cuttings.

*Disease resistance*.—Average resistance to powdery mildew (*Sphaerotheca pannosa*) and *Botrytis cinerea* diseases in a greenhouse environment in Jackson County, Oreg.

Root system:

*Type*.—Fibrous root system with many root hairs.

*Branching*.—Freely branched.

*Density*.—Densely rooted.

*Distribution*.—Moderately deep rooting.

Stems:

*Stem color*.—Both immature stems and mature stems are Green Group 137C.

*Anthocyanin intonations*.—Greyed-Purple Group 183D intonations are present on new growth only.

*Stem surface texture*.—Both immature and mature stems exhibit a smooth texture; mature stems with a few stipitate glands.

*Stem dimensions*.—Typical mature stems are approximately 15 to 18 cm long and 0.4 cm in diameter.

*Prickles*.—Incidence — Present; 13 prickles per 10 cm of stem, on average. Size — Average length is 5 to 8 mm. Immature prickle color — Green Group 137C. Mature prickle color — Greyed-Yellow Group 160D, and remaining Greyed-Yellow Group 160D at senescence. Anthocyanin intonations — Greyed-Purple Group 184C is present on immature prickles only. Shape — Deeply concave.

Leaves:

*Arrangement*.—Imparipinnate compound leaves; mature axillary leaves consisting of 5 leaflets.

*Attachment*.—Petiolate.

*Dimensions*.—118 mm long and 80 mm wide, on average.

*Abundance*.—Average.

*Stipules*.—Size — 12 to 13 mm long and 3 to 4 mm wide. Stipule color — Green Group 138A. Anthocyanin intonations — None. Stipitate glands — Abundant at margins. Margins — Serrulate, with stipitate glands. Texture, adaxial surfaces — Glabrous. Texture, abaxial surfaces — Glabrous. Apex — Aristate. Base — Winged; fused to the petiole.

*Petiole*.—Length — 15 mm. Diameter — 1.0 to 1.5 mm. Petiole color, adaxial surface — Green Group 137A. Petiole color, abaxial surface — Green Group 138A. Margins — With a limited number of stipitate glands present. Anthocyanin intonations — Greyed-Purple Group 183D present along the margins. Prickles — 1 to 2 small prickles on the abaxial surface of the petiole. Stipitate glands — Limited number of stipitate glands are present on the margins and abaxial surface. Texture — Glabrous. Strength — Moderately strong.

*Rachis*.—Length — Average 18 to 20 mm. Diameter — Average 1 mm. Color — Green Group 138B. Anthocyanin intonations — Greyed-Purple Group 183D present along the margins. Margins — Stipitate glands and very light pubescence. Prickles — A few small prickles underneath. Stipitate glands — Limited.

*Leaflets*.—Quantity — Normally 5 leaflets on normal leaves in middle of the stem. Dimensions — Average size of the terminal leaflet is 50 mm long and 30 mm wide. Shape — Ovate. Apex — Acute. Base — Round. Margins — Serrated; no undulation. Luster and texture, adaxial surface — Semi-glossy, leathery and glabrous. Luster and texture, abaxial surface — Matte, rugose, with a limited number of stipitate glands and 2 to 4 prickles on the midrib. Juvenile foliage color, adaxial surface — Green Group 137A. Juvenile foliage color, abaxial surface — Green Group 137D. Mature foliage color, adaxial surface — Green Group 139A. Mature foliage color, abaxial surface — Green Group 139C. Anthocyanin intonations — Greyed-Purple Group 184A present on abaxial surface and margins of juvenile leaflets. Venation — Reticulate. Petiolule — Dimensions — 2 mm long and 1 mm in diameter. Petiolule color, adaxial surface — Green Group 137A, with anthocyanin intonations, Greyed-Red Group 182A, at the margins. Petiolule color, abaxial surface — Green Group 137D, with anthocyanin intonations, Greyed-Red Group 182A, at the margins. Prickles — None present. Texture, adaxial surface — Smooth. Texture, abaxial surface — Smooth, with a limited number of stipitate glands. Margins — Glandular toothed and ciliate margins observed.

Inflorescence:

*Inflorescence type*.—Flowers are typically solitary.

Flowering laterals: None present.

Bud:

*Bud form*.—Long; pointed ovoid.

*Size*.—Upon opening, 28 mm in length from base of receptacle to distal end of bud and 17 mm diameter at its widest point.

*Texture*.—Smooth.

*Color, as sepals first unfold*.—Red Group 46A.

*Color when one-quarter open, inner side*.—Red-Purple Group 46A.

*Color when one-quarter open, outer side*.—Red-Purple Group 46A.

*Color when one-quarter open, outermost petals*.—Some of the outermost petals are centrally striped Yellow-Green Group 154B and suffused with Yellow-Green Group 154B in the middle zone of the petal.

Flower:

*Blooming habit*.—Recurrent; floriferous.

*Attitude of flower*.—Flowers are held upright.

*Pedicel*.—Surface — Fine hairs and stipitate glands are present. Length — 30 to 40 mm. Diameter — 1.0 to 1.5 mm. Color — Green Group 143C. Anthocyanin intonations — Greyed-Purple Group 184A. Strength — Strong. Texture — Smooth, with a moderate amount of fine hairs and stipitate glands.

*Calyx*.—General — Comprised of five polysepalous sepals, with moderate foliaceous appendages present on three of the five sepals. Diameter of calyx — 50 to 60 mm, at anthesis. Sepals — Color, adaxial surface — In between Yellow-Green Group 146A and 145B. Color, abaxial surface — Yellow-Green Group 146A. Anthocyanin intonations — Greyed-Purple Group 184A towards the distal end of immature sepals; none present on mature sepals. Size — 30 to 32 mm long and 8 to 9 mm wide, on average. Apex — Cirrose to apiculate. Base — Flat at union with receptacle. Quantity — Five. Texture, adaxial surface — With numerous fine, white hairs. Texture, abaxial surface — With a moderate amount of fine, white hairs. Margins — Entire, with a moderate amount of stipitate glands and fine, white hairs on those stipules with foliaceous appendages.

*Corolla*.—Habit; type — Double. General shape of corolla — Round. Shape of corolla when viewed from the side — Upon opening, upper portion — Convex. Upon opening, lower portion — Flattened convex. Open flower, upper portion — Flattened convex. Open flower, lower portion — Concave. Dimensions — Large for a miniature rose. When open, the average flower diameter is 45 to 55 mm and the average flower height is 35 to 40 mm. Fragrance — Light floral fragrance. Duration — On the plant 18 to 22 days. Senesced petals drop away cleanly. Petals — Petal count — 24 to 28 petals under normal conditions. Petal reflex — Slightly reflexed. Timing of petal reflex — One by one. Petal margin — Entire. Petal shape — Obovate. Apex — Obtuse. Base — Cuneate. Dimensions — 32 to 34 mm long and 30 to 32 mm wide. Texture, inner surface — Smooth. Texture, outer surface — Smooth. Petal color, upon opening — Outermost petals, outer surface — Red Group 45A. Outermost petals, inner surface — Red Group 45A. Innermost petals, outer surface — Red Group 46A. Innermost petals, inner surface — Red Group 46A. Basal petal spots, upon opening — Basal petal spot, outermost petals — Dimensions — 5 mm high and 5 mm wide. Outer surface — Yellow Group 2C. Inner surface — Yellow Group 2C. Basal petal spot, innermost petals — Dimensions — 4 mm high and 4 mm wide. Outer surface — Yellow Group 2C. Inner surface — Yellow Group 2C. Petal color, after opening — Outermost petals, outer surface — Red-Purple Group 46A. Outermost petals, inner surface — Red-Purple Group 46A. Innermost petals, outer surface — Red-Purple Group 46A. Innermost petals, inner surface — Red-Purple Group 46A. Basal petal spots, after opening — Dimensions — 7 mm high and 6 mm wide. Outer surface — Yellow Group 4A. Inner surface — Yellow Group 6A. Basal petal spot, innermost petals — Dimensions — 7 mm high and 6 mm wide. Outer surface — Yellow Group 4A. Inner surface — Yellow Group 6A. General Tonality — Red-Purple Group 57A. No change in general tonality at the end of the twelfth day. Thereafter the general tonality is Red-Purple Group 57C. Petaloids — Quantity — 6 to 10 petaloids per flower, on average. Dimensions — Highly variable; approximately 15 to 20 mm long and 5 to 10 mm wide. Color, outer surfaces — Red-Purple Group 46A; some petaloids are centrally striped Yellow Group 4A and suffused with Yellow Group 4A in the middle zone of the petal. Color, inner surfaces — Red-Purple Group 46A; some petaloids are centrally striped Yellow Group 4A and suffused with Yellow Group 4A in the middle zone of the petal. Margins — Highly irregular; entire to indented; non-undulating to undulated. Shape — Obovate. Apex — Obtuse. Base — Cuneate. Texture, inner and outer surfaces — Leathery.

Reproductive organs:

*Stamens*.—Quantity — Approximately 100 to 125, on average, and regularly arranged around the styles. Anthers — Shape — Reniform. Dimensions — 1.5 mm long and 1 mm wide, on average. Color — Yellow-Orange Group 21C. Pollen — Scarce. Pollen Color — Yellow-Orange Group 21C. Filaments — Color — Orange Group N25B. Length — 45 mm.

*Pistils*.—Quantity — Average; approximately 50 to 60. Stigmas — Dimensions — 1 mm long and 1 mm wide. Location — Slightly superior in position to anthers. Color — Yellow-Orange Group 19A. Styles — Length — Approximately 6 to 7 mm long. Color — Yellow-Orange Group 19A.

*Ovary*.—Dimensions — 4 to 5 mm long and 3 to 4 mm in diameter. Color — Yellow-Orange Group 19D.

*Receptacle*.—Shape — Urn-shaped. Dimensions — Approximately 4 mm high and 4 mm wide. Surface — Glabrous and smooth. Color — Yellow-Green Group 146B.

Hips and seed formation: Not observed.

COMPARISONS WITH THE PARENT

The new rose plant may be distinguished from its parent, 'KORpot042', by the characteristics described below in Table 1.

TABLE 1

| Characteristic | 'KORpot066' | 'KORpot042' |
|---|---|---|
| General tonality of the flower. | Red-purple Group 57A. | Red-Purple Group 65A at the center of the flower, and Red-Purple Group 65A to 65B towards the outer whorls. |
| Foliage size. | Larger than 'KORpot042'. | Smaller than 'KORpot066'. |
| General shape of the corolla. | Round. | Star shaped. |
| Flower height. | Taller than 'KORpot042'. | Shorter than 'KORpot066'. |
| Flower habit; type. | Double. | Very double. |

COMPARISON WITH THE MOST SIMILAR *ROSA* CULTIVAR KNOWN TO THE INVENTOR

For a comparison, several physical characteristics of the rose variety 'KORcarill', a rose variety from the same inventor described and illustrated in U.S. Plant Pat. No. 15,716, are compared to 'KORpot066' in Table 2.

TABLE 2

| Characteristic | 'KORpot066' | 'KORcarill' |
|---|---|---|
| Growth rate. | Moderately vigorous. | Vigorous. |
| Growth habit. | Bushier than 'KORcarill'. | Less bushy than 'KORpot066'. |
| Flower bud color, as sepals unfold. | Red Group 46A. | Red Group 52A. |
| General tonality of the flower. | Red-purple Group 57A. | Red Group 55A. |
| Flower petal count. | 24 to 28. | 34 to 38. |
| Flower lastingness. | 18 to 22 days. | 21 to 24 days. |

That which is claimed:

1. A new and distinct variety of rose plant named 'KORpot066', as described and illustrated herein.

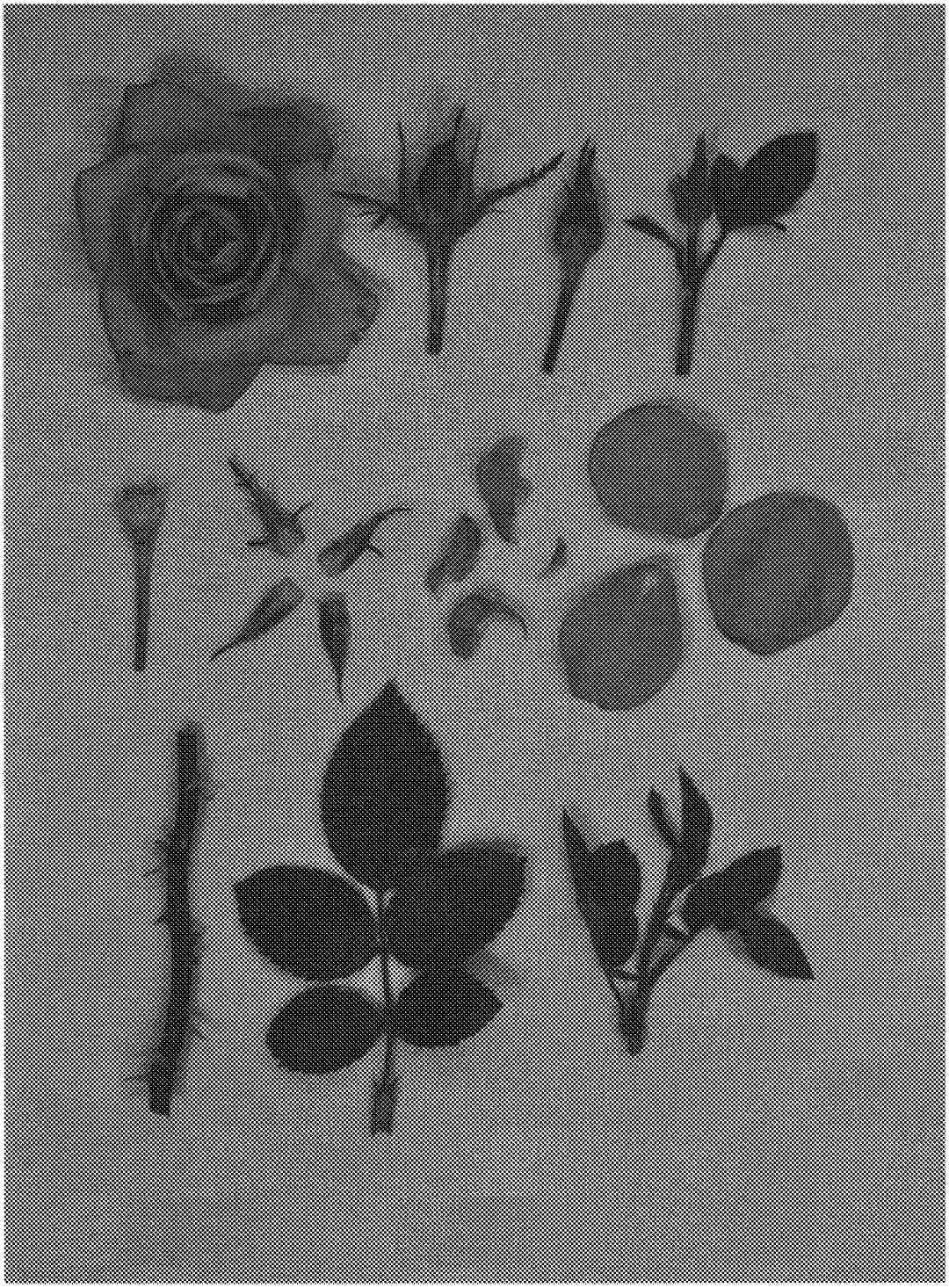

* * * * *